(12) United States Patent
Hong

(10) Patent No.: US 12,383,433 B2
(45) Date of Patent: Aug. 12, 2025

(54) FILTER AND NOISE-REDUCING EARPLUG

(71) Applicant: Mengbaolong Technology Co., Limited, Hong Kong (CN)

(72) Inventor: Huobao Hong, Hong Kong (CN)

(73) Assignee: Mengbaolong Technology Co., Limited, Hong Kong (CN)

( * ) Notice: Subject to any disclaimer, the term of this patent is extended or adjusted under 35 U.S.C. 154(b) by 211 days.

(21) Appl. No.: 18/485,781

(22) Filed: Oct. 12, 2023

(65) Prior Publication Data

US 2025/0120851 A1 Apr. 17, 2025

(51) Int. Cl.
*A61F 11/08* (2006.01)

(52) U.S. Cl.
CPC .................. *A61F 11/085* (2022.01)

(58) Field of Classification Search
CPC ................ A61F 11/06–30; A42B 3/04; A42B 3/16–166; H04R 25/00; H04R 25/65–75
See application file for complete search history.

(56) References Cited

U.S. PATENT DOCUMENTS

| | | | | |
|---|---|---|---|---|
| 3,456,263 | A * | 7/1969 | Aileo | A61F 11/14 381/372 |
| 3,795,014 | A * | 3/1974 | Simpson | A61F 11/14 381/372 |
| 2014/0373854 | A1* | 12/2014 | Keady | A61F 11/10 128/865 |
| 2018/0000649 | A1* | 1/2018 | Wang | H04R 1/1058 |
| 2020/0188176 | A1* | 6/2020 | Cran | G10K 11/162 |

* cited by examiner

*Primary Examiner* — Michelle J Lee
(74) *Attorney, Agent, or Firm* — Stein IP LLC

(57) ABSTRACT

Disclosed are a filter and a noise-reducing earplug, the noise-reducing earplug includes a filter, and the filter includes a shell, a flexible sound filtering block, and an adjustment pressing plate, wherein the shell is provided with a mounting recess and a sound outlet hole communicating with the mounting recess, the adjustment pressing plate is mounted in the mounting recess and forms a compression cavity with the mounting recess, the adjustment pressing plate is provided with sound inlet holes, the flexible sound filtering block is mounted in the compression cavity, the adjustment pressing plate contacts an end of the flexible sound filtering block away from the sound outlet hole, and the adjustment pressing plate is configured to adjust a volume of the compression cavity. The noise-reducing earplug provided in the present disclosure may adjust the noise-reducing effect; and a user may selectively filter external noise to different degrees as needed.

16 Claims, 4 Drawing Sheets

FILTER AND NOISE-REDUCING EARPLUG

TECHNICAL FIELD

The present disclosure relates to the technical field of noise-reducing devices and, more particularly, to a filter and a noise-reducing earplug.

BACKGROUND

In the prior art, the noise-reducing earplugs achieve the noise-reducing effect mainly by filters made of soft materials to directly isolate the ear canal from the ambient air. However, in different environments, users expect different levels of noise-reducing effects; for example, on the bus and airplane, a high-isolation noise-reducing effect is desirable, while at home or the workplace, a comfortable noise-reducing effect may be a moderate level. The filters in the existing noise-reducing earplugs only have a fixed noise-reducing mode, unable to adjust to a proper noise-reducing effect in response to the noise levels in different environments, thus leading to an unsatisfactory user experience.

SUMMARY

In light of the technical problem to be solved by the present disclosure, a filter and a noise-reducing earplug that may adjust the noise-reducing effect are desirable.

The technical solution of the present disclosure to solve the above-mentioned technical problem is a filter, including: a shell, a flexible sound filtering block, and an adjustment pressing plate, wherein the shell is provided with a mounting recess and a sound outlet hole communicating with the mounting recess, the adjustment pressing plate is mounted in the mounting recess and forms a compression cavity with the mounting recess, the adjustment pressing plate is provided with sound inlet holes, the flexible sound filtering block is mounted in the compression cavity, the adjustment pressing plate contacts an end of the flexible sound filtering block away from the sound outlet hole, and the adjustment pressing plate is configured to adjust a volume of the compression cavity.

In order to solve the above technical problem, the present disclosure further provides a noise-reducing earplug having the above-mentioned filter.

The present disclosure is advantageous in that: the filter and the noise-reducing earplug provided herein may adjust the noise-reducing effect; specifically, the flexible sound filtering block is provided in the compression cavity formed by the shell and the adjustment pressing plate to filter sound, and the density of the flexible sound filtering block is adjusted by operating the adjustment pressing plate to press the flexible sound filtering block, so as to achieve different sound filtering effects; and a user may selectively filter external noise to different degrees as needed.

DETAILED DESCRIPTION OF THE EMBODIMENTS

Figure 1:
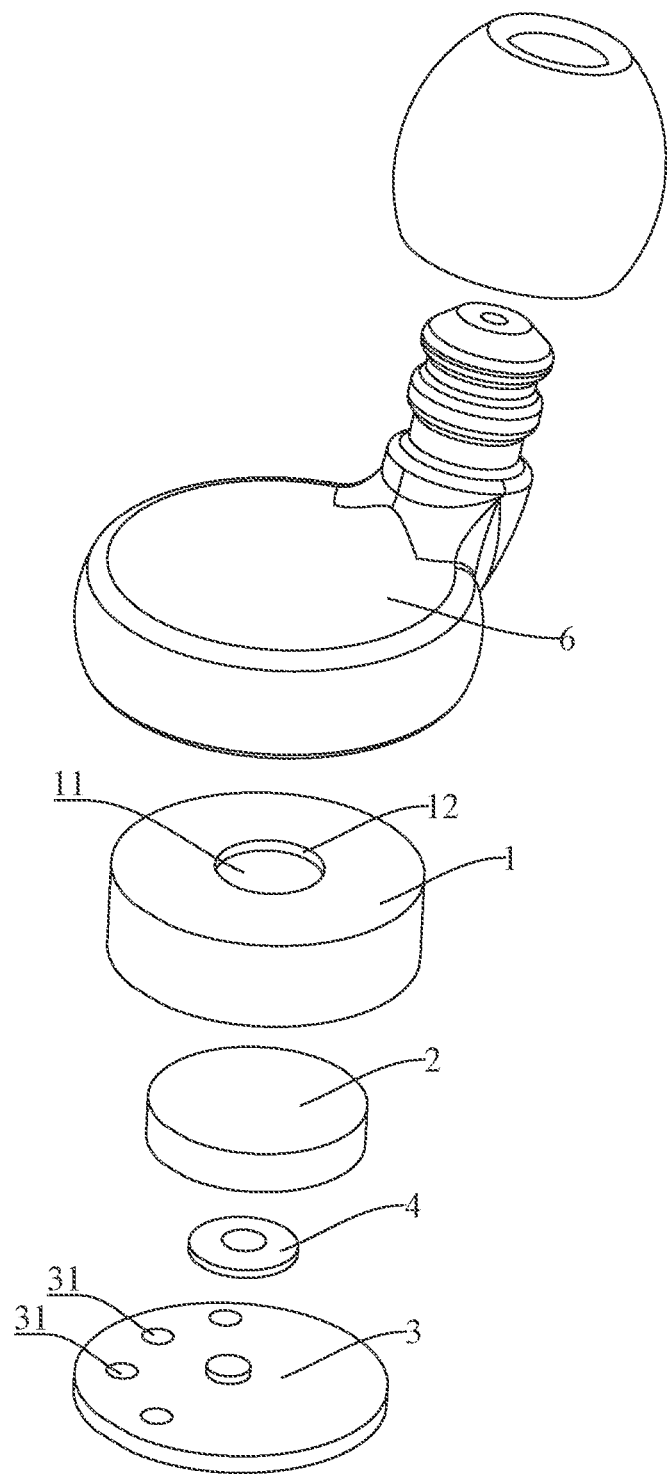
FIG. 1 is an exploded view of a noise-reducing earplug of Embodiment 1 of the present disclosure.

To explain the technical solution, object, and advantageous effects of the present disclosure in detail, the description is made below in conjunction with the embodiments and the accompanying drawings.

With reference to FIGS. 1 to 4, a noise-reducing earplug includes an earplug body 6 and a filter mounted on the earplug body 6, wherein the filter includes a shell 1, a flexible sound filtering block 2, and an adjustment pressing plate 3; the shell 1 is provided with a mounting recess 11 and a sound outlet hole 12 communicating with the mounting recess 11; the adjustment pressing plate 3 is mounted in the mounting recess 11 and forms a compression cavity with the mounting recess 11; the adjustment pressing plate 3 is provided with sound inlet holes 31; the flexible sound filtering block 2 is mounted in the compression cavity; the adjustment pressing plate 3 contacts an end of the flexible sound filtering block 2 away from the sound outlet hole 12, and the adjustment pressing plate 3 is configured to adjust a volume of the compression cavity.

It can be seen from the above description that the advantageous effects of the present disclosure are: the flexible sound filtering block 2 is provided in the compression cavity formed by the shell 1 and the adjustment pressing plate 3 to filter sound, and the density of the flexible sound filtering block 2 is adjusted by operating the adjustment pressing plate 3 to press the flexible sound filtering block 2, so as to achieve different sound filtering effects; and a user may selectively filter external noise to different degrees as needed.

Furthermore, a quantity of the sound inlet holes 31 is plural.

It can be seen from the above description that the quantity of the sound inlet holes 31 may be set according to practical application requirements.

Furthermore, the filter further includes a baffle 5 rotatably mounted to a side of the adjustment pressing plate 3 facing away from the flexible sound filtering block 2.

It can be seen from the above description that the baffle 5 may block part or all of the sound inlet holes 31, and an exposed area of the sound inlet holes 31 is adjusted by rotating the baffle 5, thereby further adjusting the sound filtering effect.

Furthermore, the adjustment pressing plate 3 is further provided with a guide inserting shaft 33, and a side wall of the guide inserting shaft 33 is provided with an elastic snap 34; a guide shaft sleeve 13 is provided in the mounting recess 11, and an inner side wall of the guide shaft sleeve 13 is provided with a plurality of stroke slots 14; the stroke slots 14 are evenly distributed along a length direction of the guide shaft sleeve 13.

It can be seen from the above description that the movement of the adjustment pressing plate 3 in the mounting recess 11 may be guided by the cooperation between the guide inserting shaft 33 and the guide shaft sleeve 13, thereby ensuring that the adjustment pressing plate 3 may stably press the flexible sound filtering block 2.

Furthermore, the flexible sound filtering block 2 is provided with a clearance 21 for the guide shaft sleeve 13 and the guide inserting shaft 33 to avoid each other.

It can be seen from the above description that the clearance 21 may allow the guide shaft sleeve 13 and the guide inserting shaft 33 to avoid each other.

Furthermore, a side wall of the adjustment pressing plate 3 is provided with an external thread, and a side wall of the mounting recess 11 is provided with an internal thread mating with the external thread.

Furthermore, the adjustment pressing plate 3 is further provided with a threaded inserting shaft, and a threaded sleeve is provided in the mounting recess 11; the threaded inserting shaft is in threaded connection with the threaded sleeve.

It can be seen from the above description that by providing the adjustment pressing plate 3 in the threaded connection with the shell 1, the position in movement of the adjustment pressing plate 3 in the mounting recess 11 may be adjusted more accurately, and the accuracy of adjusting the sound filtering effect may be improved.

Furthermore, the flexible sound filtering block 2 is provided with an clearance 21 for the threaded shaft sleeve and the threaded inserting shaft to avoid each other.

It can be seen from the above description that the clearance 21 may allow the threaded shaft sleeve and the threaded inserting shaft to avoid each other.

Furthermore, an end of the adjustment pressing plate 3 facing away from the flexible sound filtering block 2 is provided with a knob 32.

It can be seen from the above description that the knob 32 facilitates a user rotating the adjustment pressing plate 3.

Furthermore, the adjusting pressing plate 3 is provided with a rotating plate 4, and the rotating plate 4 contacts the flexible sound filtering block 2.

It can be seen from the above description that the rotating plate 4 may prevent the adjustment pressing plate 3 from rubbing against the flexible sound filtering block 2 during rotation, reducing the risk of twisting the flexible sound filtering block 2.

Embodiment 1

Figure 2:
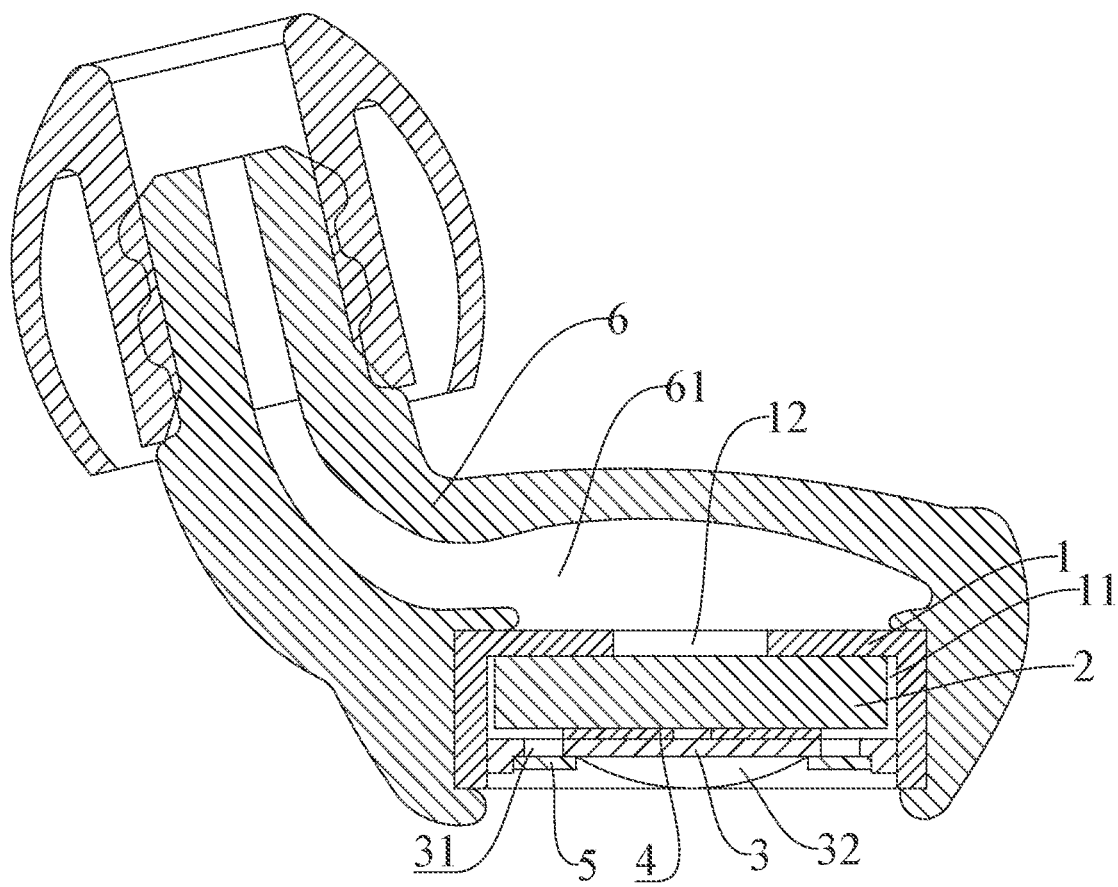
FIG. 2 is a schematic cross-sectional view of the noise-reducing earplug according to Embodiment 1 of the present disclosure.

With reference to FIGS. 1 and 2, Embodiment 1 of the present disclosure is as follows. A noise-reducing earplug includes an earplug body 6 and a filter mounted on the earplug body 6, wherein the filter includes a shell 1, a flexible sound filtering block 2, and an adjustment pressing plate 3. The earplug body 6 is provided with a sound channel 61, and the shell 1 is mounted in the sound channel 61; the shell 1 is provided with a mounting recess 11 and a sound outlet hole 12 in communication with the mounting recess 11, and the sound outlet hole 12 is in communication with the sound channel 61; the adjustment pressing plate 3 is mounted in the mounting recess 11 and forms a compression cavity with the mounting recess 11; the adjustment pressing plate 3 is provided with sound inlet holes 31, and the flexible sound filtering block 2 is mounted in the compression cavity; specifically, the flexible sound filtering block 2 is made of a sponge material, a rubber material, or a foam rubber material, which may be specifically determined according to actual application requirements; the adjustment pressing plate 3 contacts an end of the flexible sound filtering block 2 away from the sound outlet hole 12; the adjustment pressing plate 3 is configured to adjust the volume of the compression cavity; the flexible sound filtering block 2 is provided in the compression cavity formed by the shell 1 and the adjustment pressing plate 3 to filter sound; the density of the flexible sound filtering block 2 is adjusted by operating the adjustment pressing plate 3 to press the flexible sound filtering block 2, so as to achieve different sound filtering effects; and a user may selectively filter external noise to different degrees as needed.

Optionally, the quantity of the sound inlet holes 31 is plural, and the quantity of the sound inlet holes 31 may be specifically set according to actual application requirements; specifically, the noise-reducing earplug further includes a baffle 5, and the baffle 5 is rotatably mounted on a side of the adjustment pressing plate 3 facing away from the flexible sound filtering block 2; the sound inlet holes 31 are arranged on the way of the baffle 5 when rotating, and the baffle 5 may block part or all of the sound inlet holes 31, with an exposed area of the sound inlet holes 31 adjusted by rotating the baffle 5, so as to further adjust the sound filtering effect; more specifically, the baffle 5 is provided with an adjusting hole for aligning with the sound inlet hole 31, and the baffle 5 is rotated so that the adjusting hole is aligned or misaligned with the sound inlet hole 31, thereby controlling the sound inlet holes 31 to be opened and closed.

In this embodiment, the adjustment pressing plate 3 is rotatably connected to the shell 1; optionally, a side wall of the adjustment pressing plate 3 is provided with an external thread, and a side wall of the mounting recess 11 is provided with an internal thread mating with the external thread; alternatively, the adjustment pressing plate 3 is provided with a threaded inserting shaft (not shown), and a threaded shaft sleeve (not shown) is provided in the mounting recess 11, with the threaded inserting shaft in threaded connection with the threaded shaft sleeve; the flexible sound filtering block 2 is provided with a clearance 21 for the threaded shaft sleeve and the threaded inserting shaft to avoid each other, and the clearance 21 may allow the threaded shaft sleeve and the threaded inserting shaft to avoid each other. By providing the adjustment pressing plate 3 in the threaded connection with the shell 1, the position in movement of the adjustment pressing plate 3 in the mounting recess 11 may be adjusted more accurately, and the accuracy of adjusting the sound filtering effect may be improved.

Preferably, an end of the adjustment pressing plate 3 facing away from the flexible sound filtering block 2 is provided with a knob 32, and the knob 32 facilitates a user rotating the adjustment pressing plate 3; specifically, the adjusting pressing plate 3 is further provided with a rotating plate 4, and the rotating plate 4 contacts the flexible sound filtering block 2. The rotating plate 4 may prevent the adjustment pressing plate 3 from rubbing against the flexible sound filtering block 2 during rotation, reducing the risk of twisting the flexible sound filtering block 2.

Embodiment 2

Figure 3:
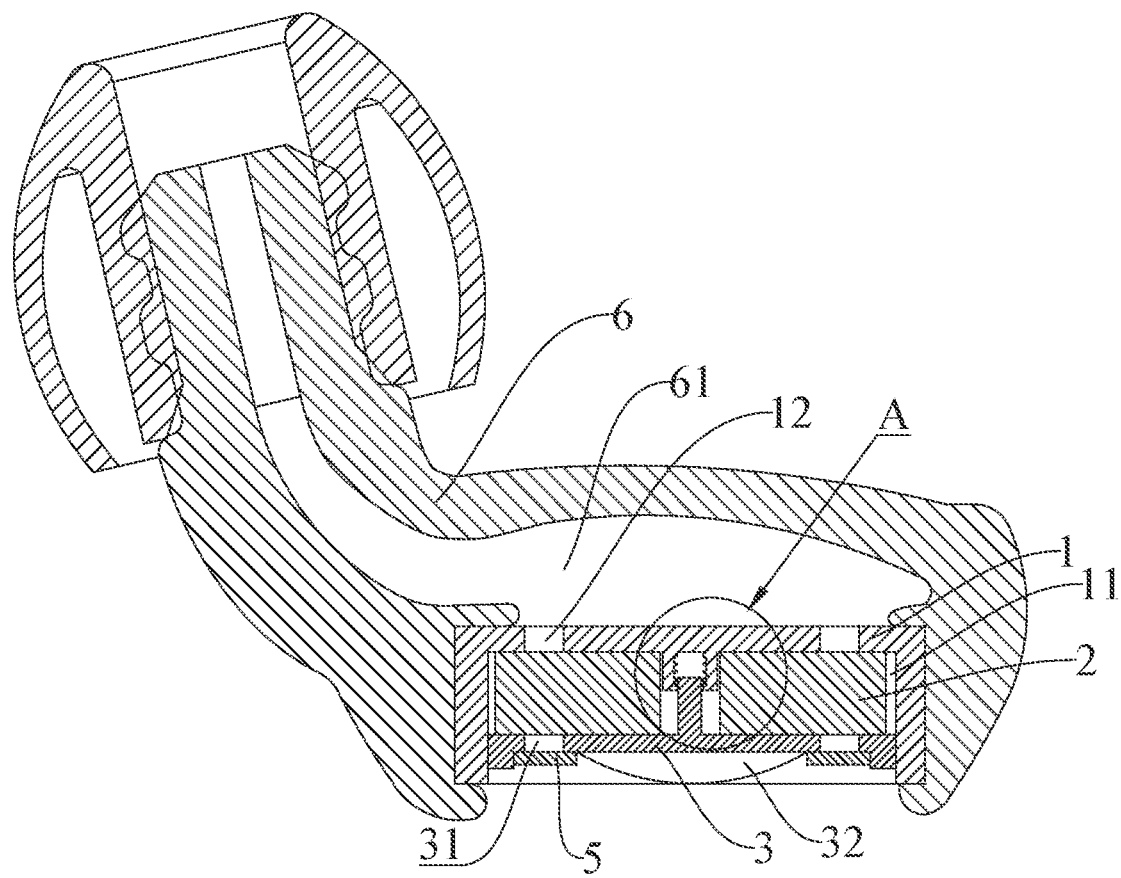
FIG. 3 is a schematic cross-sectional view of the noise-reducing earplug according to Embodiment 2 of the present disclosure.
Figure 4:
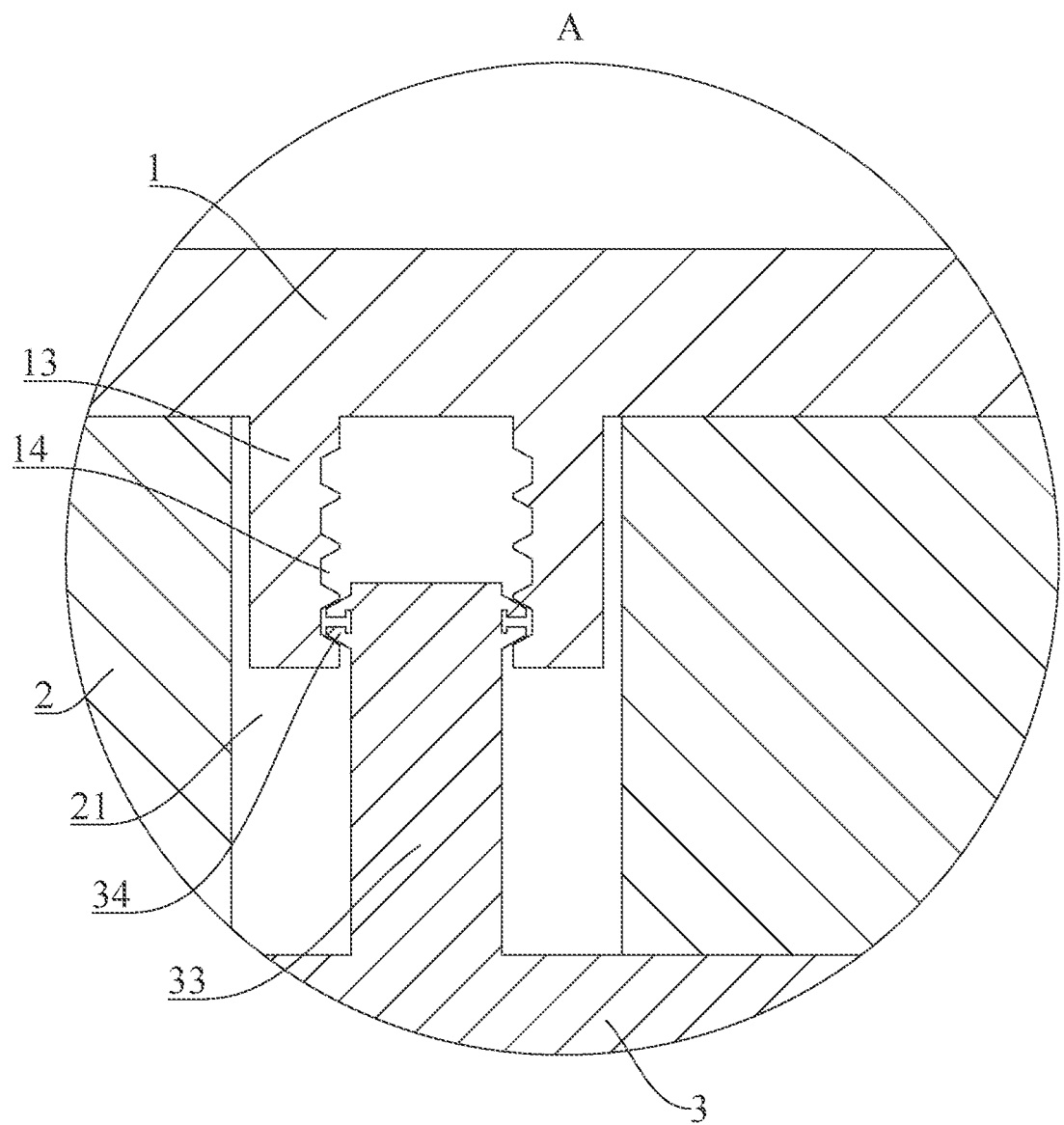
FIG. 4 shows details at A in FIG. 3.

Referring to FIGS. 3 and 4, Embodiment 2 of the present disclosure differs from Embodiment 1 in that the adjustment pressing plate 3 is operated differently. In this embodiment, the density of the flexible sound filtering block 2 is adjusted by pressing the adjustment pressing plate 3; the adjustment pressing plate 3 is provided with a guide inserting shaft 33, and a side wall of the guide inserting shaft 33 is provided with an elastic snap 34; the mounting recess 11 is provided with a guide shaft sleeve 13, and an inner side wall of the guide shaft sleeve 13 is provided with a plurality of stroke slots 14; the stroke slots 14 are evenly distributed along a length direction of the guide shaft sleeve 13. The movement of the adjustment pressing plate 3 in the mounting recess 11 may be guided by the cooperation between the guide inserting shaft 33 and the guide shaft sleeve 13, thereby ensuring that the adjustment pressing plate 3 may stably press the flexible sound filtering block 2. Specifically, the flexible sound filtering block 2 is provided with a clearance 21 for the guide shaft sleeve 13 and the guide inserting shaft 33 to avoid each other, and the clearance 21 may allow the guide shaft sleeve 13 and the guide inserting shaft 33 to avoid each other.

In summary, the filter and the noise-reducing earplug provided herein may adjust the noise-reducing effect; specifically, the flexible sound filtering block is provided in the compression cavity formed by the shell and the adjustment pressing plate to filter sound, and the density of the flexible sound filtering block is adjusted by operating the adjustment pressing plate to press the flexible sound filtering block, so as to achieve different sound filtering effects; and a user may selectively filter external noise to different degrees as needed.

The above description is only examples of the present disclosure, and is not intended to limit the patent scope of the present disclosure. All equivalent variations based on the description and drawings of the present disclosure, directly or indirectly used in related technical fields, shall equally fall within the scope of the present disclosure.

What is claimed is:

1. A filter, comprising: a shell, a flexible sound filtering block, and an adjustment pressing plate, wherein the shell is provided with a mounting recess and a sound outlet hole communicating with the mounting recess, the adjustment pressing plate is mounted in the mounting recess and forms a compression cavity with the mounting recess, the adjustment pressing plate is provided with sound inlet holes, the flexible sound filtering block is mounted in the compression cavity, the adjustment pressing plate contacts an end of the flexible sound filtering block away from the sound outlet hole, and the adjustment pressing plate is configured to adjust a volume of the compression cavity, wherein the adjustment pressing plate is further provided with a threaded inserting shaft extending through a center of the filtering block, the mounting recess is provided with a threaded shaft sleeve, and the threaded inserting shaft is in threaded connection with the threaded shaft sleeve to adjust a density of the filtering block.

2. The filter according to claim 1, wherein a side wall of the threaded inserting shaft is provided with an elastic snap, an inner side wall of the threaded shaft sleeve is provided with a plurality of stroke slots, and the plurality of stroke slots are uniformly distributed along a length direction of the threaded shaft sleeve.

3. The filter according to claim 2, wherein the flexible sound filtering block is provided with a clearance for the threaded shaft sleeve and the threaded inserting shaft to avoid each other.

4. The filter according to claim 1, wherein a quantity of the sound inlet holes is plural.

5. The filter according to claim 1, further comprising: a baffle rotatably mounted to a side of the adjustment pressing plate facing away from the flexible sound filtering block.

6. The filter according to claim 1, wherein the flexible sound filtering block is provided with a clearance for the threaded shaft sleeve and the threaded inserting shaft to avoid each other.

7. The filter according to claim 1, wherein an end of the adjustment pressing plate facing away from the flexible sound filtering block is provided with a knob.

8. The filter according to claim 1, wherein the adjustment pressing plate is further provided with a rotating plate that contacts the flexible sound filtering block.

9. A noise-reducing earplug, comprising an earplug body and a filter mounted to the earplug body, wherein the filter comprises a shell, a flexible sound filtering block, and an adjustment pressing plate, the shell is provided with a mounting recess and a sound outlet hole communicating with the mounting recess, the adjustment pressing plate is mounted in the mounting recess and forms a compression cavity with the mounting recess, the adjustment pressing plate is provided with sound inlet holes, the flexible sound filtering block is mounted in the compression cavity, the adjustment pressing plate contacts an end of the flexible sound filtering block away from the sound outlet hole, and the adjustment pressing plate is configured to adjust a volume of the compression cavity, wherein the adjustment pressing plate is further provided with a threaded inserting shaft extending through a center of the filtering block, the mounting recess is provided with a threaded shaft sleeve, and the threaded inserting shaft is in threaded connection with the threaded shaft sleeve to adjust a density of the filtering block.

10. The noise-reducing earplug according to claim 9, wherein a side wall of the threaded inserting shaft is provided with an elastic snap, an inner side wall of the threaded shaft sleeve is provided with a plurality of stroke slots, and the plurality of stroke slots are uniformly distributed along a length direction of the threaded shaft sleeve.

11. The noise-reducing earplug according to claim 10, wherein the flexible sound filtering block is provided with a clearance for the threaded shaft sleeve and the threaded inserting shaft to avoid each other.

12. The noise-reducing earplug according to claim 9, wherein a quantity of the sound inlet holes is plural.

13. The noise-reducing earplug according to claim 9, further comprising a baffle rotatably mounted to a side of the adjustment pressing plate facing away from the flexible sound filtering block.

14. The noise-reducing earplug according to claim 9, wherein the flexible sound filtering block is provided with a clearance for the threaded shaft sleeve and the threaded inserting shaft to avoid each other.

15. The noise-reducing earplug according to claim 9, wherein an end of the adjustment pressing plate facing away from the flexible sound filtering block is provided with a knob.

16. The noise-reducing earplug according to claim 9, wherein the adjustment pressing plate is further provided with a rotating plate that contacts the flexible sound filtering block.

* * * * *